United States Patent
D'Alessio et al.

(10) Patent No.: US 6,494,896 B1
(45) Date of Patent: Dec. 17, 2002

(54) APPLICATOR FOR LAPAROSCOPIC OR ENDOSCOPIC SURGERY

(75) Inventors: Keith R. D'Alessio, Cary, NC (US); Lawrence H. Mainwaring, Raleigh, NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 09/450,686

(22) Filed: Nov. 30, 1999

(51) Int. Cl.⁷ ............................................... A61B 17/04
(52) U.S. Cl. ........................ 606/213; 604/19; 604/36; 604/38
(58) Field of Search ............................ 606/213; 604/19, 604/36, 38

(56) References Cited

U.S. PATENT DOCUMENTS

| | | |
|---|---|---|
| 2,765,332 A | 10/1956 | Coover, Jr. et al. |
| 3,483,870 A | 12/1969 | Coover, Jr. et al. |
| 3,524,537 A | 8/1970 | Winter |
| 3,527,224 A | 9/1970 | Rabinowitz |
| 3,527,841 A | 9/1970 | Wicker, Jr. et al. |
| 3,559,652 A | 2/1971 | Banitt et al. |
| 3,564,078 A | 2/1971 | Wicker, Jr. et al. |
| 3,667,472 A | 6/1972 | Halpern |
| 3,722,599 A | 3/1973 | Robertson et al. |
| 3,940,362 A | 2/1976 | Overhults |
| 3,995,641 A | 12/1976 | Kronenthal et al. |
| 4,237,871 A | 12/1980 | Bonnet |
| 4,479,933 A | 10/1984 | Akimova et al. |
| 4,526,173 A | 7/1985 | Sheehan |
| 4,637,380 A | 1/1987 | Orejola |
| 5,047,047 A | 9/1991 | Yoon |
| 5,222,939 A | 6/1993 | Tiefenbrun et al. |
| 5,236,440 A | 8/1993 | Hlavacek |
| 5,263,971 A | 11/1993 | Hirshowitz et al. |
| 5,281,197 A | 1/1994 | Arias et al. |
| 5,312,333 A | 5/1994 | Churinetz et al. |
| 5,314,406 A | 5/1994 | Arias et al. |
| 5,372,585 A | 12/1994 | Tiefenbrun et al. |
| 5,397,332 A | 3/1995 | Kammerer et al. |
| 5,415,631 A | 5/1995 | Churinetz et al. |
| 5,456,388 A | 10/1995 | Honstein et al. |
| 5,529,577 A | 6/1996 | Hammerslag ............... 606/214 |
| 5,531,760 A | 7/1996 | Alwafaie |
| 5,549,565 A | 8/1996 | Ryan et al. |
| 5,562,705 A | 10/1996 | Whiteford |
| 5,665,817 A | 9/1997 | Greff et al. |
| 5,692,642 A * | 12/1997 | Brattesani ..................... 222/1 |
| 6,004,547 A | 12/1999 | Rowe et al. |

\* cited by examiner

Primary Examiner—Gary Jackson
(74) Attorney, Agent, or Firm—Oliff & Berridge, PLC (57) ABSTRACT

A hand-held applicator delivers liquid or semi-liquid compositions, such as adhesives, to an internal tissue or organ in an even and controlled manner. The applicator includes a pump, a tubular extension that is thin enough to pass through an endoscopic pathway or trocar, a proximal end of the tubular extension being sealingly connected to the pump, and an applicator tip that attaches to the distal end of the tubular extension. The tip includes the liquid and the pump pumps the liquid to the internal tissue in an even and controlled manner without contact of the liquid by the pump. The pump is preferably a micropipetter that includes a hand-held portion having a hand-actuatable plunger that does not come in direct, physical contact with the liquid to be dispensed. The composition may be an adhesive such as an alpha-cyanoacrylate. The device may further include a wound closure device including at least two closure pins extending from the distal end of the tubular extension. The wound closure device retracts from the applicator device and orients and aligns a wound or incision target tissue site immediately prior to application of the medical composition. The device provides improved control, ergonomics, and convenience. The device is particularly useful in the field of surgery, especially in the field of laparoscopic or endoscopic surgery, where an even and controlled amount of a medically-acceptable adhesive is to be applied to a target site on an internal tissue or organ.

45 Claims, 7 Drawing Sheets

APPLICATOR FOR LAPAROSCOPIC OR ENDOSCOPIC SURGERY

BACKGROUND OF THE INVENTION

This invention relates to the field of surgery and wound closure. More particularly, this invention relates to devices for applying medically-acceptable adhesives, such as 1,1-disubstituted ethylene monomers, to surgical sites.

Medical adhesives are used as alternates and/or adjuncts to sutures and staples as wound closure devices. As used herein, "wound" encompasses all disruptions of animal tissue, regardless of manner inflicted, and includes, for example, wounds that are inflicted unintentionally, through surgery, and through natural causes (e.g., degeneration of tissue, infection, etc.) One group of medical adhesives is the monomeric forms of 1,1-disubstituted ethylene monomers, such as α-cyanoacrylates. Members of this group are disclosed in, for example, U.S. Pat. Nos. 5,328,687 to Leung et al; U.S. Pat. No. 3,527,841 to Wicker et al.; U.S. Pat. No. 3,722,599 to Robertson et al.; U.S. Pat. No. 3,995,641 to Kronenthal et al.; and U.S. Pat. No. 3,940,362 to Overhults.

Applying medically acceptable adhesives to surgical sites for wound closure requires that the adhesive be dispensed in a precise and controlled manner to the site. Medical practitioners have encountered problems in applying this type of adhesive to internal organs and other deep tissues due to the current limited ability to evenly and controllably dispense an appropriate and accurate amount of the desired adhesive to the site to be closed. Although devices for delivering substances to wound sites are known in the art, none of the devices provide an adequate means for delivering a predetermined amount of adhesive to the site in a controlled and even manner.

For example, U.S. Pat. Nos. 5,222,939 and 5,372,585 to Tiefenbrun et al. disclose laparoscopic instruments that comprise a receptacle for storing a predetermined amount of a biologically active composition, and an ejector to mechanically inject the composition into a surgical site. These instruments rely on a piston to contact the biologically active composition and drive it through an elongated shaft of the laparoscopic instrument onto the site.

U.S. Pat. Nos. 5,312,333 and 5,415,631 to Churnitz et al. disclose endoscopic devices for delivering a metered quantity of material to an intended site of application within a body. The devices comprise a containment reservoir containing the material to be delivered either in the handle or at the endoscopic portion of the device. The devices utilize either a plunger which makes contact with the containment reservoir, or a propellant which forces the material from the distal end of the endoscopic devices.

U.S. Pat. No. 4,237,871 to Bonnet discloses a device for injecting pastes or fluid substances into human obturation organs by means of an injection tube which is axially displaceable through an endoscope shaft. The device disclosed by Bonnet utilizes a cylinder which is filled from the proximal end of the device with the fluid or paste to be delivered. The fluid or paste is then forced out of the cylinder by contact with a piston, which is actuated forward by the use of a mechanical screw thread. The piston causes delivery of the fluid or paste by exerting direct physical compressive force which forces the fluid or paste to extrude through the injection tube and thus to the site of interest.

U.S. Pat. No. 5,281,197 to Arias et al. discloses an endoscopic tool for repetitive dispensing of discrete units of a hemostatic agent The device disclosed by Arias et al. incorporates a hollow tube endoscopic device into which a plurality of individual, discrete units of a hemostatic agent is incorporated. The tool utilizes incremental movements of a plunger to contact the proximal most discrete unit and dispense the individual units of the agent.

U.S. Pat. No. 5,456,388 to Honstein et al. discloses a hand-held dispenser for delivering adhesives. The device disclosed by Honstein et al. comprises a cylindrical barrel containing a column of fluid or semi-fluid adhesive, and a cylindrical piston in direct contact with this column of fluid. Adhesive is dispensed from the device by rotation of a thumbwheel that is connected to the piston through a threaded rod. Turning the thumbwheel causes the piston to move against the fluid, resulting in displacement of the fluid and delivery of the fluid to a surface to be bonded.

Additionally, besides the difficulty in obtaining a precise amount of adhesive to internal organs and other deep tissues, it has been difficult to properly align and orient a wound or incision at such sites immediately prior to and during the adhesive application.

SUMMARY OF THE INVENTION

The present invention relates to a medical device for delivering liquid or semi-liquid compositions, such as adhesives, to an internal tissue or organ in an even and controlled manner. The device broadly comprises a pump, a tubular extension that is thin enough to pass through an endoscopic pathway or trocar, a proximal end of the tubular extension being sealingly connected to the pump, and an applicator tip that attaches to the distal end of the tubular extension. The tip includes the controlled amount of liquid and the pump pumps the liquid to the internal tissue in an even and controlled manner without contact of the liquid by the pump.

In a preferred embodiment, the pump comprises a micropipetter that includes a hand-held portion having a hand-actuatable plunger that does not come in direct, physical contact with the liquid to be dispensed. However, the invention can be practiced by lesser accuracy pumps such as syringes, diaphragms, gas pumps or pressurized gas pumps.

The present invention also relates to a method of use of the device to dispense a controlled amount of the composition to a site.

In another embodiment of the invention, the medical delivery device is further provided with a wound closure device.

The devices and methods of the present invention are particularly useful in the field of surgery, especially in the field of laparoscopic or endoscopic surgery where an even and controlled amount of a medically-acceptable adhesive is to be applied to a site on an internal tissue or organ The devices and methods provide improved control, ergonomics, and convenience compared to devices and methods currently known.

The use of medical delivery devices and wound closure devices of the present invention can provide even further control and effectiveness in the field of surgery, particularly laparoscopic or endoscopic surgery, as an internal wound or incision can be properly aligned and oriented at the site immediately prior to and during the adhesive application.

DETAILED DESCRIPTION OF PREFERRED EMBODIMENTS

The present invention relates to a device and method for delivery of a controlled amount of a liquid or semi-liquid composition to a surface. In embodiments, the device is useful for delivery of medically-acceptable adhesives to wound sites, such as sites created from surgical incisions or other surgical procedures. In all embodiments, the device comprises a pump that pumps a controlled amount of a liquid or semi-liquid composition, which preferably is a monomeric adhesive, e.g., a 1,1-disubstituted ethylene adhesive such as an α-cyanoacrylate adhesive. The device further comprises a tubular assembly connected to a distal end of the pump at a proximal end of the tubular assembly. The tubular assembly includes a seal housing and a tubular extension that is thin enough and long enough to pass through an endoscopic pathway or trocar. The device fisher comprises a reuseable or replaceable tip that attaches to a distal end of the tubular assembly.

The present invention also relates to a method of using the device and includes the steps of inserting the device into a laparoscopic pathway or trocar extending into a body, positioning the tip adjacent target tissue within the body, activating the pump to controllably dispense the composition onto the tissue through the tip, and removing the device from the laparoscopic pathway or trocar.

The pump preferably includes a piston or plunger operably linked to a control area. The linkage is preferably mechanical. In the case where the linkage is mechanical, the piston may, for example, be linked to a button through a push rod made of any suitable material, such as metal or plastic, for example. Preferably, a working fluid, such as air or another gas, is used to transfer the pumping action of the pump to the distal end of the tubular assembly. As such, there is no direct contact between the pump and the dispensed composition, such as an adhesive. In one embodiment, when actuated, the plunger moves towards the distal end of the assembly and applies pressure to the working fluid. The compression of the working fluid then causes the medical fluid to dispense out of the distal end of the assembly. When a high precision pump is used, such as a micropipetter, a high precision application of a medical fluid can be applied to a surgical site.

The pump may be covered by a protective casing made of any suitable material. Suitable protective casing materials for the pump include, but are not limited to, plastics, metals, and synthetic rubbers. The materials used in the casing and pump are preferably able to withstand at least one type of sterilization technique known to the skilled artisan so that the device can be used in a sterile medical environment. Preferable sterilization techniques include, but are not limited to, chemical, physical, and irradiation methods. Examples of chemical methods include, but are not limited to, exposure to ethylene oxide or hydrogen peroxide vapor, and exposure to alcohol (ethanol or isopropanol). Examples of physical methods include, but are not limited to, moist heat sterilization and dry heat sterilization. Examples of irradiation methods include, but are not limited to, gamma irradiation, electron beam irradiation, and microwave irradiation.

The tubular assembly comprises a hollow tubular extension that should have an outer diameter small enough to fit within a laparoscopic pathway or trocar, yet have an inner bore diameter large enough for a sufficient amount of a working gas or liquid to flow to transfer the pressure generated by the pump to the tip such that an even and controlled amount of liquid can be dispensed. The diameters can be modified based on the requirements for each application, as long as the inner bore diameter remains sufficiently large to function in accordance with the invention. For example, the outer diameter of the tubular assembly can be increased or decreased depending on the inner diameter of the laparoscopic pathway or trocar. The tubular assembly should have a length that is sufficiently long to extend through the laparoscopic pathway or trocar to the wound site. The length of the tubular assembly can be selected according to the needs for each application. From a practical standpoint, however, the length of the tubular structure will typically be between 15–61 cm, for example, 23 to 46 cm or 23 to 36 cm and the outer diameter will typically be between 1 to 15 mm, for example 3 to 12 mm or 4 to 8 mm. The tubular structure can be made of any suitable material, preferably one that can withstand at least one sterilization technique known to the skilled artisan, such as those that are useful for sterilization of the pump disclosed above.

Figure 1:
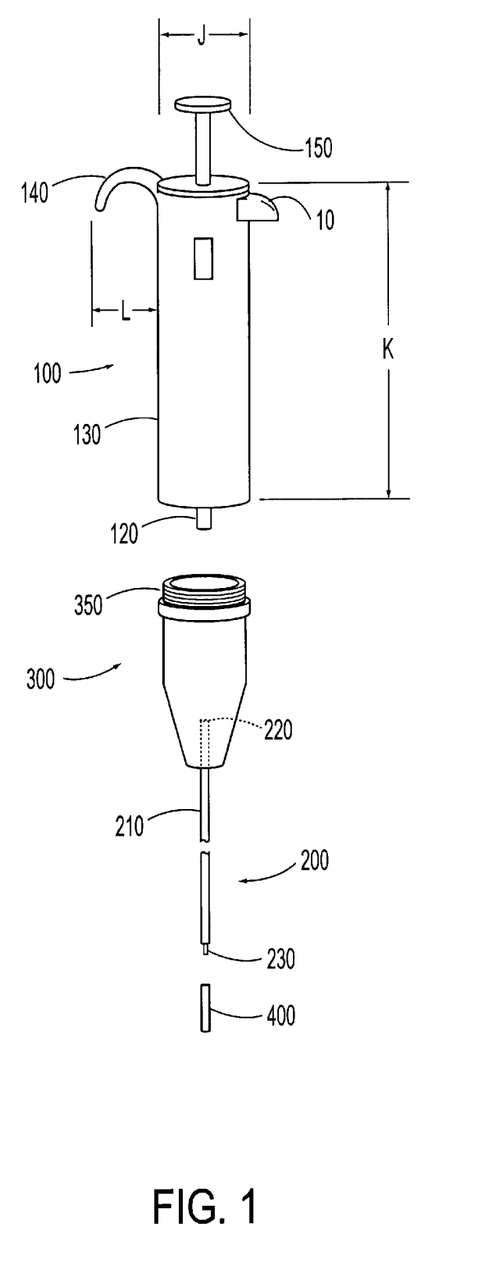
FIG. 1 shows a perspective view of a device according to one embodiment of the invention.
Figure 2:
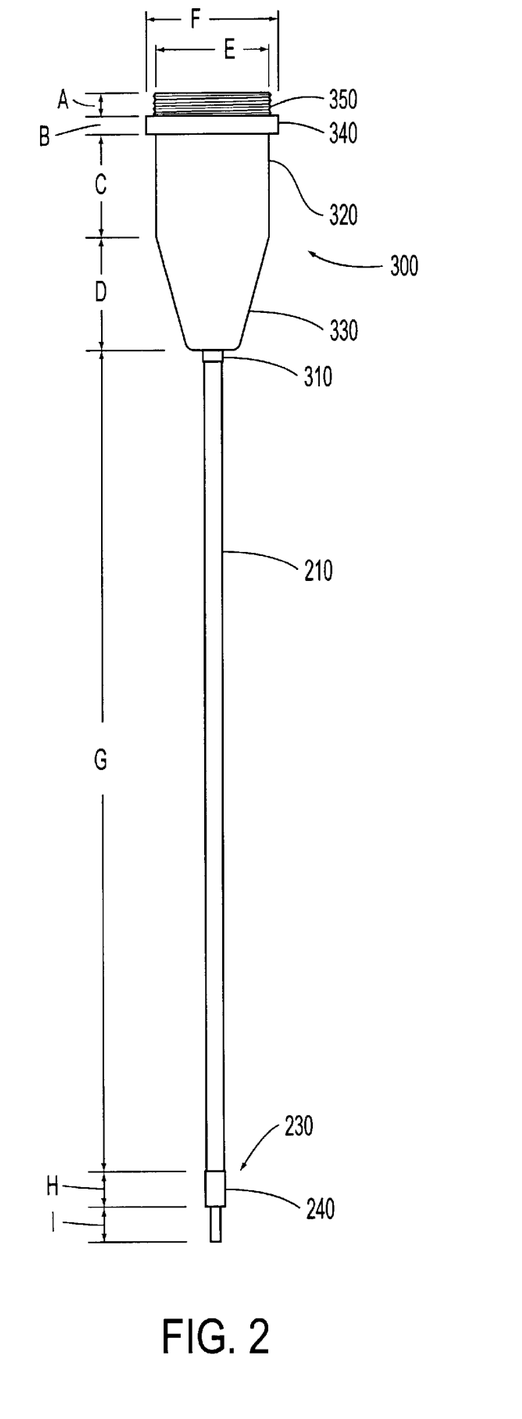
FIG. 2 shows a side view of an exemplary seal housing and tubular extension used in conjunction with the first embodiment of the invention.
Figure 3:
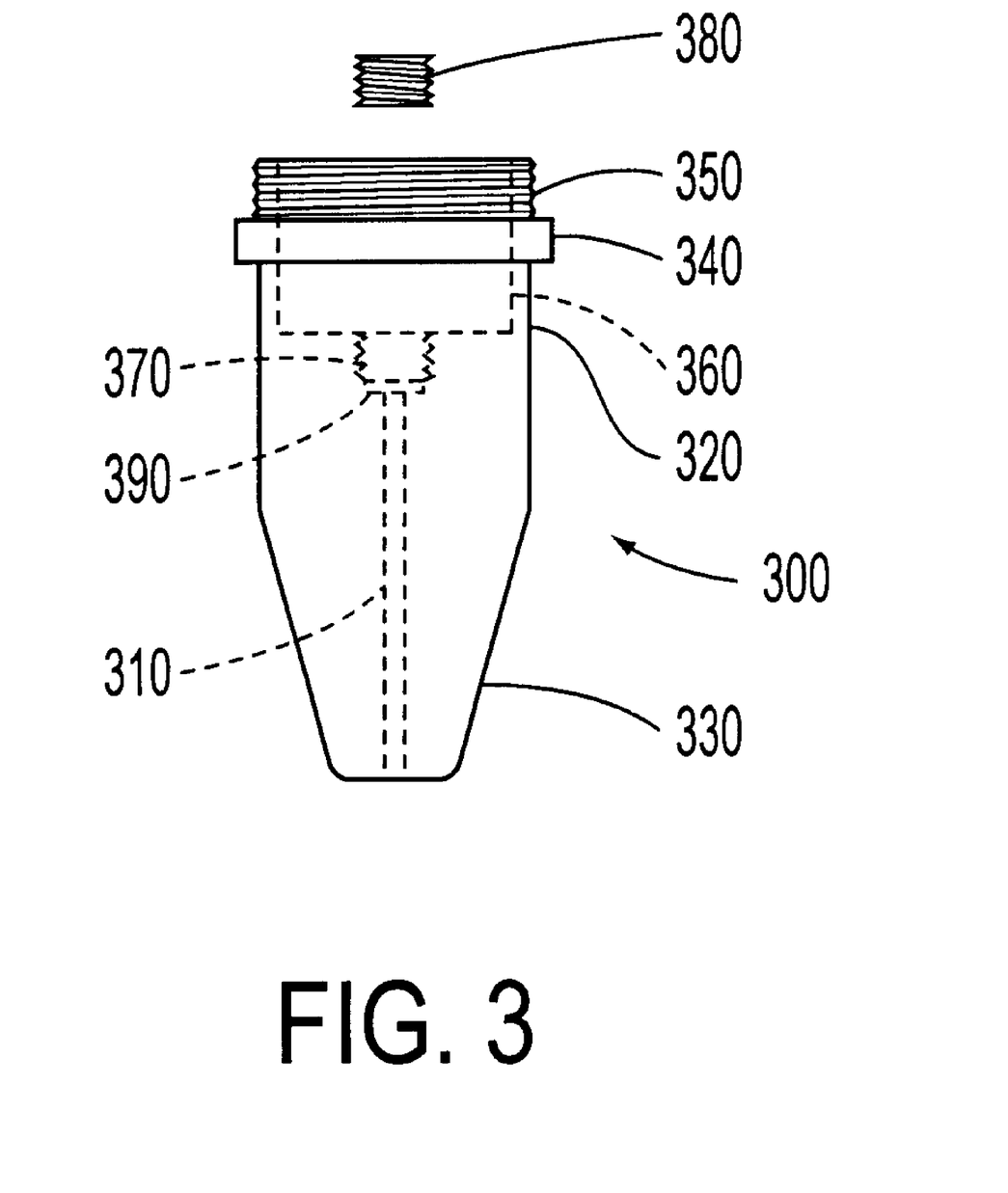
FIG. 3 shows an enlarged side view of a suitable seal housing.

In a first embodiment, as shown in FIGS. 1–3, the device comprises a pump 100 that pumps a controlled amount of a medical composition, which preferably is a monomeric adhesive, e.g., a 1,1-disubstituted ethylene adhesive such as an α-cyanoacrylate adhesive. A particularly suitable pump 100 is a pipetter. However, other suitable pumps, including but not limited to syringes, can serve as alternative devices. Such alternative devices may or may not have the same degree of controllability that can be achieved through use of a pipetter. However, depending on the particular application, such accuracy may not be necessary.

The pipetter of FIG. 1 includes a plunger 150 externally extended from a base 130, a handle 140, and a distal end 120 that is designed to be received by a reuseable macrotip (unshown). The base 130 is grippable by a hand of a user and the plunger 150 can be actuated by one or more fingers or a thumb of the user while gripping the base 150. As such, operation of the pump device can be achieved with single hand use. An optional lever 700 can be provided to activate an additional function, which will be described later with reference to FIGS. 10–21.

Numerous commercially available pipetters are available in a large variety of sizes from companies such as VWRbrand, Vangard, Brinmann, Eppendorf, and SMI. They can include mechanical or visual gauges or preferably include a digital display for more precise control in dispensing the composition. An exemplary pipetter is a Calibra Digital micropipetter from VWRbrand having a dispensing range of between 20–200 $\mu$L, an incremental volume adjustment of 10 $\mu$L, and an accuracy of +/−0.7%. This particular micropipetter includes a stainless steel and plastic plunger 150, a lightweight base 130, a handle 140, a distal end 120, and lever 700. This pipetter has a base with a height K of about 11 cm and a diameter J of about 3 cm. The handle 140 has an inner diameter L of about 2.5 cm and is designed as a stop that abuts against a pointer finger of the user.

While this particular exemplary pump is a single pipetter, the invention can also be practiced using a repeat (multi) pipetter.

The device further comprises a tubular assembly 200 connected to the distal end 120 of the pump 100 (pipetter) at a proximal end 220 of the tubular assembly 200. The tubular assembly 200 comprises a tubular extension 210 that is thin enough and long enough to pass through an endoscopic pathway or trocar. The device further comprises a replaceable tip 400 that attaches to a distal end 230 of the tubular assembly 200.

This exemplary embodiment is particularly suitable for use with a 5 mm trocar, such as trocars available from Ethicon Endosurgery of Cincinnati, Ohio and Tyco Healthcare (United States Surgical operating unit) of Norwalk, Conn. However, the invention can be adapted for use with any trocar simply by changing specific dimensions of some of the elements, particularly the outer diameter and length of tubular extension 210 and the length and width of pump 100.

A seal housing 300 is located between base 130 and tubular extension 200. An exemplary seal housing 300 has a 5 mm aperture 310, a main body 320 with a length C of about 1.5 cm, a tapering body 330 with a length D of about 1.7 cm, a lip 340 with a height B of about 0.75 cm, and a threaded portion 350 with a height of about 0.75 cm. The threaded portion 350 has a diameter E of about 2.2 cm and is sized to thread onto a corresponding internal thread of the pump, which in this embodiment is micropipetter 100. The overall diameter F of seal housing 300 is about 2.6 cm. A large end of seal housing 300 opposite aperture 310 is open to define a cavity 360 sized slightly smaller than outer diameter E. A stepped portion 370 is located between and in fluid communication with cavity 360 and aperture 310. The diameter of stepped portion 370 is larger than aperture 310. Preferably, at least a portion of stepped portion 370 is internally threaded for receiving a threaded member 380, which is used to retain a sealing member 390. A suitable sealing member 390 may be formed from one or more O-rings, preferably two O-rings. Sealing member 390 serves to seal the internal cavity 360 and the tubular assembly 200 so that the proximal end 220 of the tubular assembly 200 connects to the distal end 120 of the pump device 100, making an airtight seal between the two that can withstand the pressure of insufflation, which typically is between 10 to 15 mm Hg.

Tubular assembly 200 can be made of any suitable material including, but not limited to metal, plastic, and rubber. In this particular embodiment, tubular extension 210 comprises a stainless steel tube having an outside diameter of 0.50 cm and a length G of about 20.2 cm. To ensure adequate sealing, particularly when used with a metal tubular extension, the proximal end 220 of the tubular assembly 200 can include two O-rings 390. However, one of skill in the art could make any number of variations, as long as the proximal end 220 is connected to the distal end 120 of the pump device 100 making an airtight seal that can withstand the pressure of insufflation, which typically is between 10 to 15 mm Hg. Moreover, the tubular assembly is not to be limited to the specific sizes and lengths described with respect to specific applications. Instead, the tubular assembly 200 in its broadest sense can be of any size and length sufficient to connect with the pump device 100 to provide a sealed attachment and of a length sufficient to extend the distal end 230 of the tubular assembly 200 beyond a particular trocar to be used.

The distal end 230 of tube assembly 200 in this embodiment includes a plastic member 240 affixed to the stainless steel tube 210 (FIG. 2). The outer diameter of plastic member 240 is also 0.50 cm at one end, but a distal end of plastic member 240 (forming distal end 230 of tubular assembly 200) preferably has a reduced diameter, such as 0.40 cm, that is sized to accept a replaceable tip 400 and allows retention of replaceable tip 400 by friction fit. A length I of the reduced diameter portion is about 0.65 cm and the length H of the wider portion is about 1.2 cm. In this embodiment, the inner diameter of the replaceable tip 400 would likewise be 0.4 cm (preferably nominally smaller) to ensure friction fit.

The tubular assembly 200 can be attached to the distal end 120 of pump device 100 by any suitable means including, but not limited to, glue and mechanical fasteners (e.g., luer locks, threads). The entire tubular assembly 200 can also be fabricated as a single unit, with all of the elements being integrally incorporated into the assembly. For example, the entire tubular assembly can be manufactured as a single item from plastic rather than a composite tubular assembly having steel, plastic and rubber O-ring components.

Figure 4:
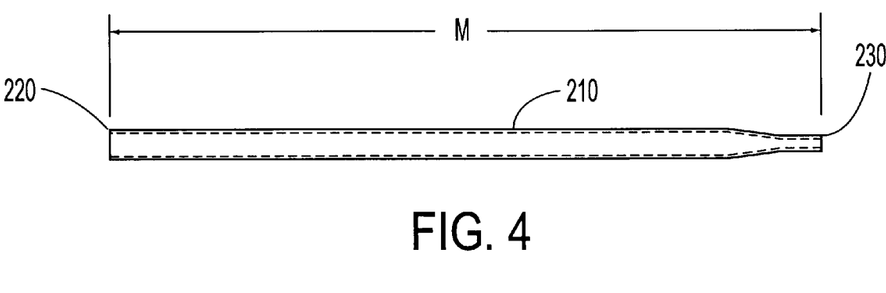
FIG. 4 shows a side view of an exemplary tubular extension according to the first embodiment of the invention.
Figure 5:
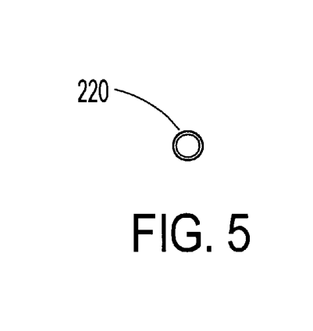
FIG. 5 shows a left end view of the tubular extension of FIG. 4.
Figure 6:
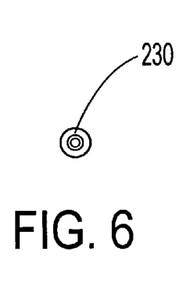
FIG. 6 shows a right end view of the tubular extension of FIG. 4.

A tubular assembly 200 according to a second embodiment of the invention is shown in FIGS. 4–5. In this embodiment, tubular extension 210 has a length M of between 11.4–14.0 cm (4.5–5.5"), an outer diameter of about 0.57 cm (0.225") and an inner diameter of about 0.23 cm (0.09"). Distal end 230 is tapered or stepped to have a reduced outer diameter of about 0.4 cm (0.150"). Preferably, distal end 230 forms a taper lock that frictionally fits into the tip 400, to removably fix the tip in place. That is, the distal end 230 is frustoconical so as to fit by friction into a conical opening in the end of tip 400. Due to the taper, the farther the distal end is inserted into the conical opening, the higher the frictional force applied to the tip to retain it in place.

Preferred types of tips 400 may include tips that can deliver a fine bead of adhesive (e.g., around 0.5 millimeters), a broad width of adhesive (e.g., several millimeters), or a fine spray of adhesive with similar coverage. The tips of the present invention can be made of any suitable material, preferably one that can be sterilized without losing function. The tips can be made from materials including, but not limited to, polypropylene, polyethylene and Pyrex (glass). Preferably, however, the tips are made of polyethylene. The tips are also preferably, but not necessarily, sterilized and disposable. The tips can be sterilized by any technique known to the skilled artisan, such as those discussed previously.

In a preferred embodiment, tip 400 is filled with a liquid composition, packaged, then sterilized. The sterilized tip and liquid composition therein are then removed from the packaging by a user, and attached directly to the distal end 230 of the tubular assembly 200 just prior to use. The tips 400 can contain a volume of the composition in any amount, for example between 1 to 1000 μL, and preferably between 20 to 200 μL.

The tip 400 attaches to the tubular assembly in such a way that an airtight seal is created, for example between the inside surface of the tip and the outside surface of the tubular assembly. One such method of attachment is a frictional fit between the tip 400 and the distal end 230 of the tubular assembly 200. For example, the inside diameter of the proximal (with respect to the tubular extension) end 410 of the tip 400 can be slightly smaller than the outside diameter of the distal end 230 of the tubular assembly 200. The distal end 230 of the tubular assembly 200 can be inserted into the proximal end 410 of the tip 400 with slight pressure. Inserting of the distal end 230 into the tip 400 in such a way results in an airtight seal between the tubular extension and the tip, and allows the tip to be attached to the tubular extension without any further fastening means. Alternative attachments can include screw threads, luer locks, bayonet style attachments and the like.

In preferred embodiments, the tip is detachable and disposable. It is also contemplated that several different types of tips can be designed and used in conjunction with this device in order to meet the needs of a wide range of uses. All such design variations are encompassed by this invention.

Figure 7:
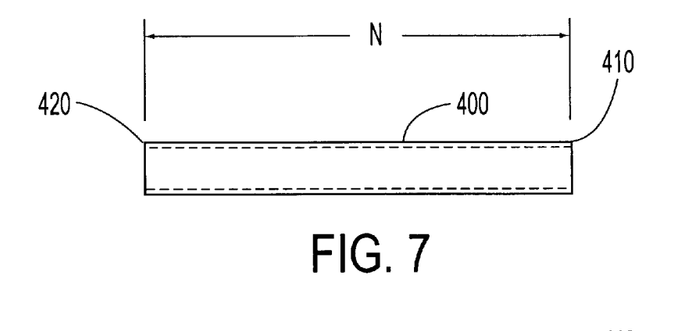
FIG. 7 shows a side view of an exemplary reuseable tip according to the invention.
Figure 8:
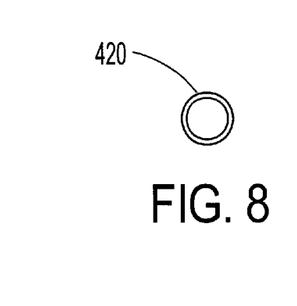
FIG. 8 shows an end view of the reuseable tip of FIG. 7.

In one exemplary embodiment, shown in FIGS. 7 and 8, tip 400 preferably has a length N of about 4.45 cm, an inner diameter of about 0.4 cm, and an outer diameter of about 0.57 cm. The tip is preferably made of porous polyethylene. Both proximal end 410 and distal end 420 have the same dimensions in this embodiment.

Figure 9:
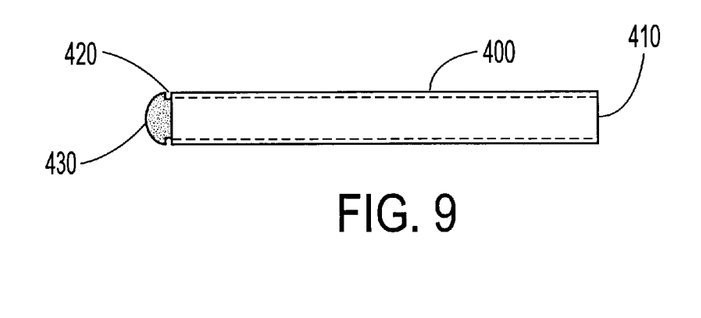
FIG. 9 shows a tip according to a second embodiment of the invention.

In another exemplary embodiment shown in FIG. 9, tip 400 includes a porous end member 430, such as porous polyethylene.

The composition to be delivered with the device can be any composition that is liquid or semi-liquid. Preferable compositions comprise medically-acceptable adhesives, such as 1,1-disubstituted ethylene monomers, such as alpha-cyanoacrylates.

In preferred embodiments of the invention, when the composition is an alpha-cyanoacrylate, the tip 400 may have on or in it a polymerization initiator or rate modifier, e.g., accelerator or inhibitor, which assists the cyanoacrylate adhesive to polymerize quickly and completely as well as allowing the operator to apply the adhesive in several successive layers which will be advantageous for applications requiring high tensile strength. The tip may additionally or alternatively contain a bioactive material. Examples of applicator tips useable in the present invention can be found in U.S. Pat. No. 5,928,611 and co-pending U.S. patent application Ser. No. 09/069,979 filed Apr. 30, 1998, and patent application Ser. No. 09/176,889 filed Oct. 22, 1998, the disclosures of which are incorporated herein by reference in their entirety.

In a preferred embodiment, a tip is filled with a cyanoacrylate monomer solution, packaged, then sterilized. The sterilized tip, containing adhesive, is then attached directly to the tubular extension just prior to use, such as by friction fitting. The tip can include sealed foil "caps" that are punctured for use. In this case, a mechanism may be provided to expel displaced air. This can be achieved, for example, by having a button that leaks air to the outside of the casing during tip assembly. This could operate similar to a turkey baster button. Alternatively, the monomer solution could be vacuum loaded into the tip.

With respect to FIGS. 10–21, a third embodiment of the invention will be described, which is particularly useful in application of an adhesive to an internal tissue site, such as a wound or incision. In this embodiment, the hand held applicator further includes a wound closure device that facilitates proper alignment and closure of the wound or incision prior to the application of the adhesive.

Like numerals refer to like elements. The overall hand-held applicator is similar to previously described embodiments and includes a pump 100, a tubular extension 200, and a seal housing 300. However, this embodiment further includes a second, larger tubular extension 500, which coaxially surrounds tubular extension 200 and provides a free space therebetween for receiving a wound closure device made up of two or more retractable, preferably telescopic, wound closure pins 600, which are actuatable through manipulation of a manipulation element, such as lever 700, provided on pump 100.

Figure 10:
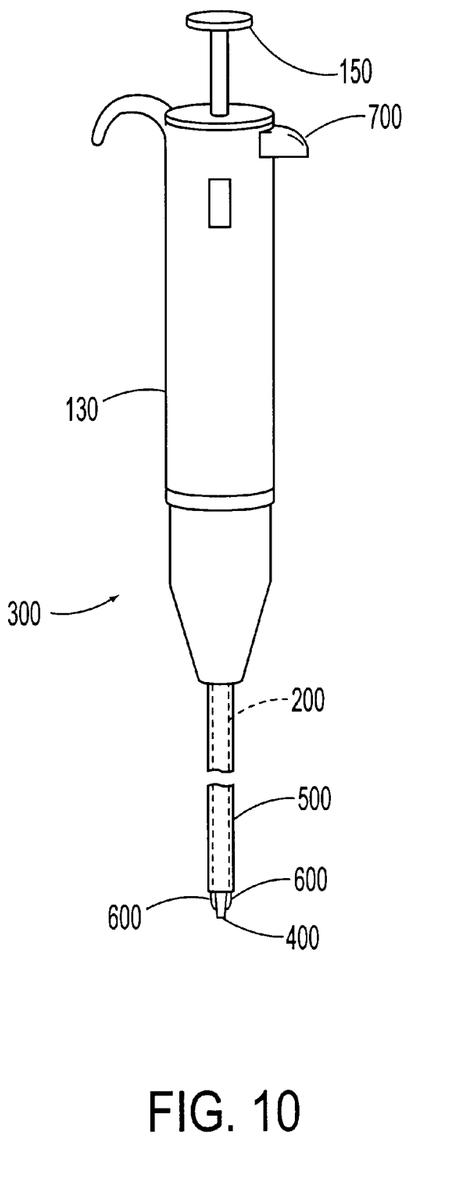
FIG. 10 shows a perspective view of a device according to a third embodiment of the invention with a wound closure device in a first position.
Figure 11:
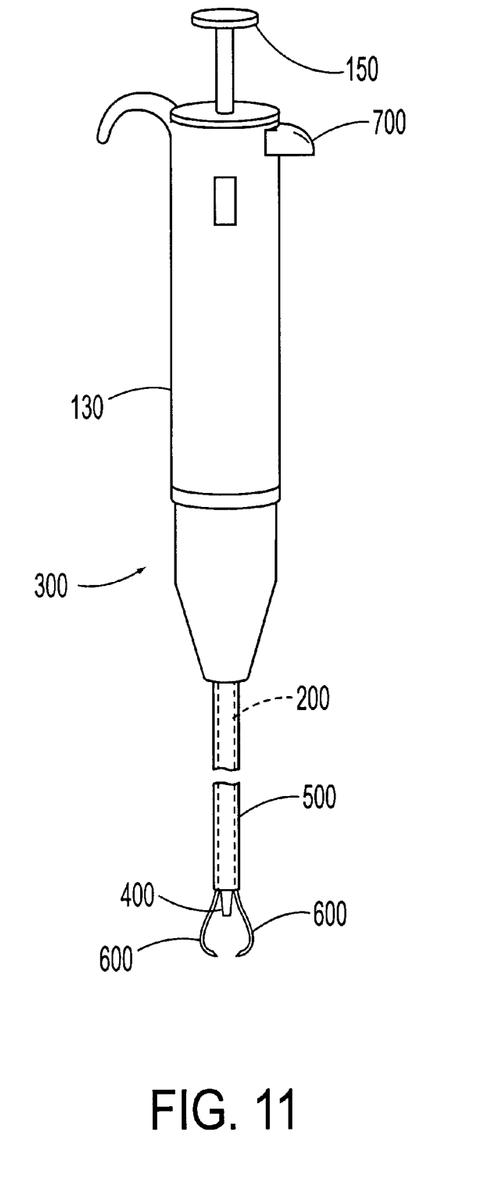
FIG. 11 shows a perspective view of the device of FIG. 10 with the wound closure device in a second position.

As shown in FIG. 10, pins 600 are initially retracted and either slightly inside or slightly outside of a distal end of tubular extension 500. However, when the lever 700 is actuated, as shown in FIG. 11, pins 600 extend outwardly from the distal end of tubular extension 500. As better shown in FIGS. 12–13, pins 600 can be mechanically coupled to lever 700 through a base ring 610 and a connecting element 620, which is of a suitable semi-rigid or rigid material such as metal or plastic. Connecting element 620 is sized to movably fit in the coaxial gap formed between tubular extension 200 and tubular extension 500. Pins 600 can be formed of a suitable material, such as plastic or metal and may preferably be formed from a spring steel so as to be resilient, allowing them to conform to the size constraints of the coaxial gap during retraction, yet allowing expansion of the pins upon extension. Pins 600 are sized to penetrate tissue and aid in closing of a wound or incision.

Figure 12:
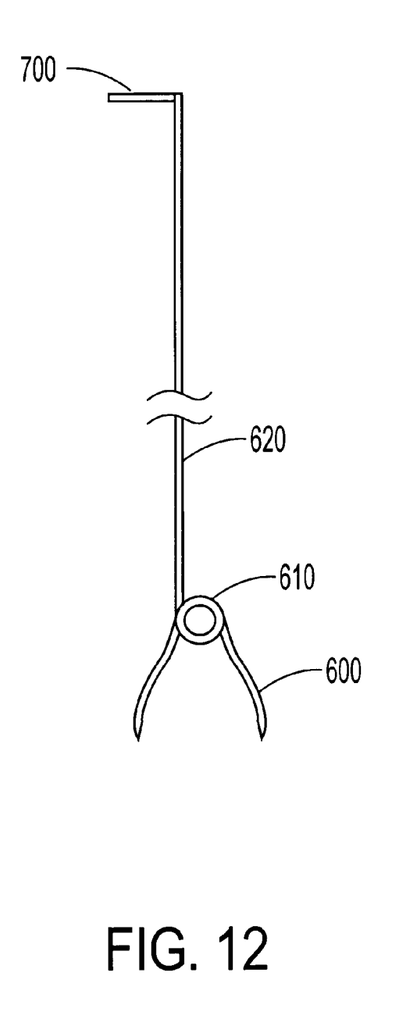
FIG. 12 shows a more detailed view of an exemplary activation mechanism for the wound closure device shown in FIGS. 10–11.
Figure 13:
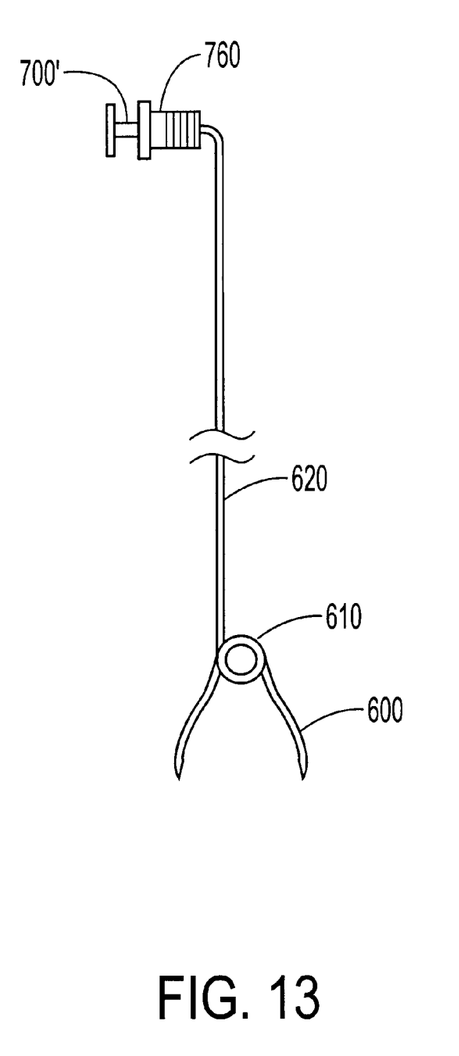
FIG. 13 shows a more detailed view of an alternative activation mechanism for the wound closure device shown in FIGS. 10–11.

In FIG. 12, lever 700 moves with the connecting element 620 to retract or extend the pins 600. Alternatively, as shown in FIG. 13, a push button 700' can serve as a manipulation element, which can be attached to pump 100, seal housing 300 or elsewhere so long as it is convenient for operator manipulation and connectable with pins 600 through connecting element 620. Lever 700 preferably includes a ratcheting mechanism to allow the force of the wound closure device to be adjusted and held. This would free up the hands of the operator to apply the formulation and hold the wound in place as the glue polymerizes. Any of many conventional ratcheting devices can be used for this purpose.

In operation, as the lever 700 is depressed, it will hold in any position unless released by a mechanical device. The operator can then slowly move the lever until the wound is closed. When the operator releases the lever, it will remain in place, holding the wound closed. The operator then applies the adhesive and waits for it to sufficiently polymerize while the pins 600 and lever 700 remain in position. After polymerization, the operator operates a release mechanism to free the lever and the pins.

Figure 21:
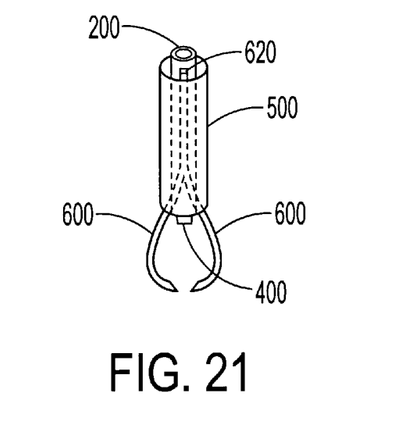
FIG. 21 shows a close up of the end of the wound closure device of FIG. 20.

When the wound closure device is contained within the hand-held applicator, it is desirable to retain the sealed environment. As such, the connections between seal housing 300 and base 130 should be sealed. Moreover, the manipulation element 700 should be suitably sealed. Alternative arrangements that do not require such sealing can be achieved if the wound closure device is external to the hand-held applicator, such as that shown in FIG. 20 where the connecting element 620 and manipulation element 700 are fed into tubular extension 500 downstream from seal housing 300. As such, the original seal between tubular extension 200, seal housing 300 and base 130 can be retained as in earlier embodiments. Alternatively, the tubular extension 500 can be eliminated and the collar 610 and pins 600 can be provided externally about the tubular extension 200. Additionally, besides pins 600 being retained on a collar 610, they can be commonly attached for pivotal movement about a pivot pin, such as shown in FIG. 21.

Figure 14:
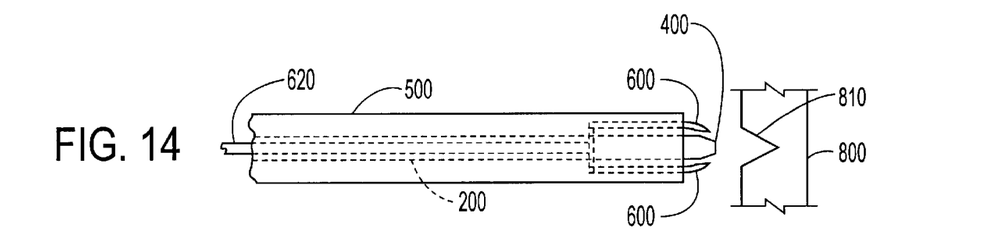
FIGS. 14–18 show use of the device of the third embodiment to close a surgical wound on a surgical tissue site.
Figure 17:
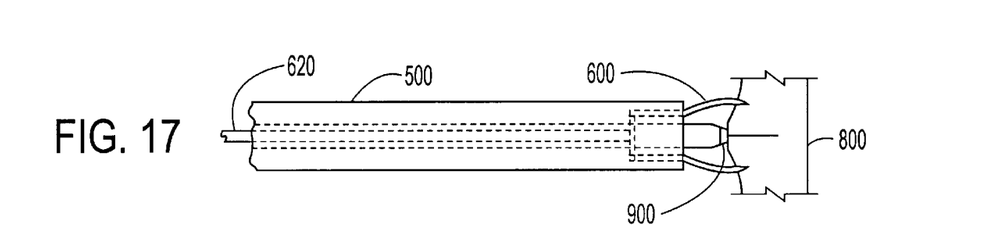
Figure 18:
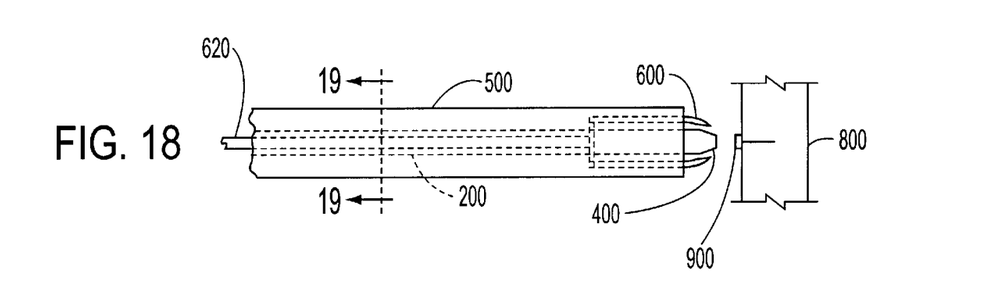
Figure 19:
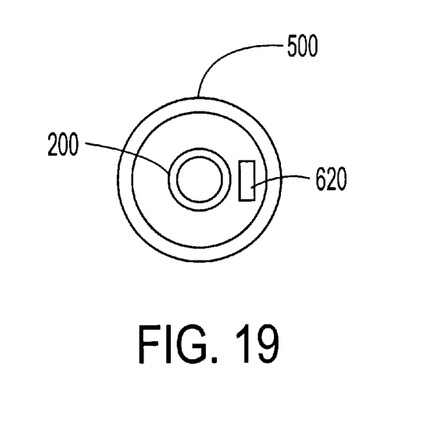
FIG. 19 shows a cross-sectional view of the device of FIG. 18 taken along line 19—19.
Figure 20:
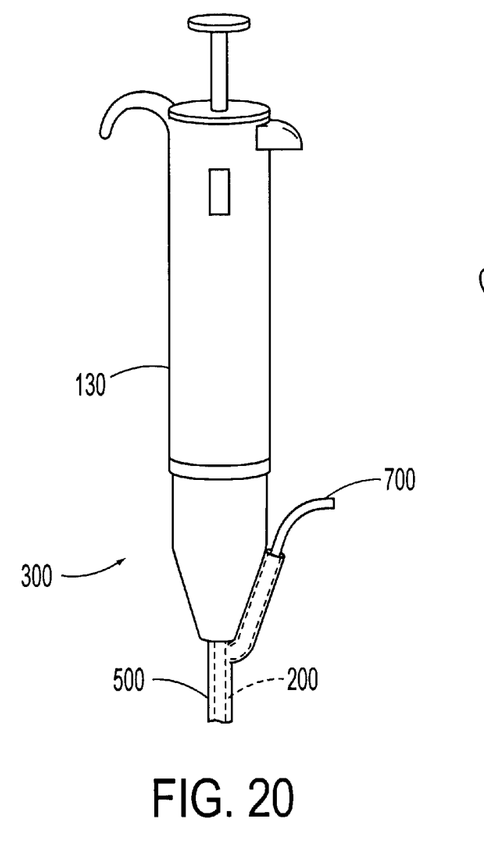
FIG. 20 shows an alternative actuation mechanism of the wound closure device.

An exemplary alignment and adhesive application process, such as that used during endoscopic or laparoscopic surgery, will be described with reference to FIGS. 14–19. FIG. 19 shows a cross-sectional view of the tubular extensions 200 and 500, with connecting element 620 extending therebetween. In FIG. 14, tubular extensions 200 and 500 of the applicator are shown adjacent a target tissue 800. Before this step, the hand-held applicator has been sterilized and loaded with a predetermined amount of adhesive in tip 400. Then, the tip 400 and tubular extensions 200 and 500 of the hand-held applicator are inserted through a laparoscopic pathway or trocar. As shown, pins 600 are initially retracted to a position near a distal end of the applicator. As illustrated, the target tissue 800 can include a wound or incision 810 that is desired to be closed by the applicator.

Incisions tend to separate as shown, forming a V-shape. Before and/or after application of the adhesive from the hand-held applicator, it is desirable to close the incision so that it can properly heal. This may be achieved by the inventive wound closure device.

Figure 15:
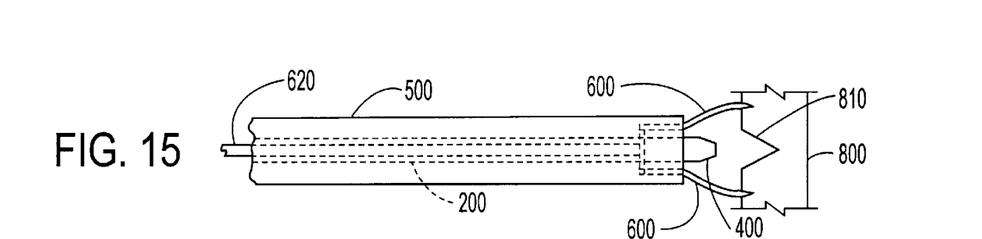
Figure 16:
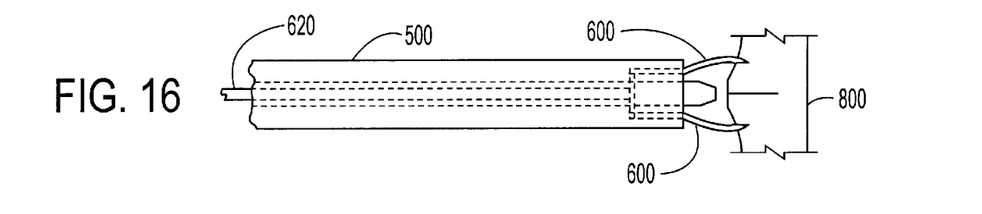

As shown in FIG. 15, the pins 600 are extended to penetrate the target tissue 800 adjacent the incision 810. This can be achieved, for example, by manipulation of the lever 700, which causes connecting element 620 to act on and extend the pins 600. As shown, it is preferable that the closure pins spread out or initially be spaced radially outward from tubular extension 500. Then, as shown in FIG. 16, pins 600 are at least partially retracted, again by manipulation of the lever 700. In the process, the pins move radially inward. This draws the target tissue around the incision 810 inward and closes and aligns the incision to a condition that is now ready for bonding by the adhesive. The plunger of the hand-held applicator can be actuated to dispense a predetermined amount of the adhesive contained within tip 400 onto the incision to form one or more sutureless adhesive strips 900 directly on the incision as shown in FIG. 17. Then, as shown in FIG. 18, the pins 600 are fully retracted and the hand-held applicator is moved away from the target tissue 800.

Figure 22:
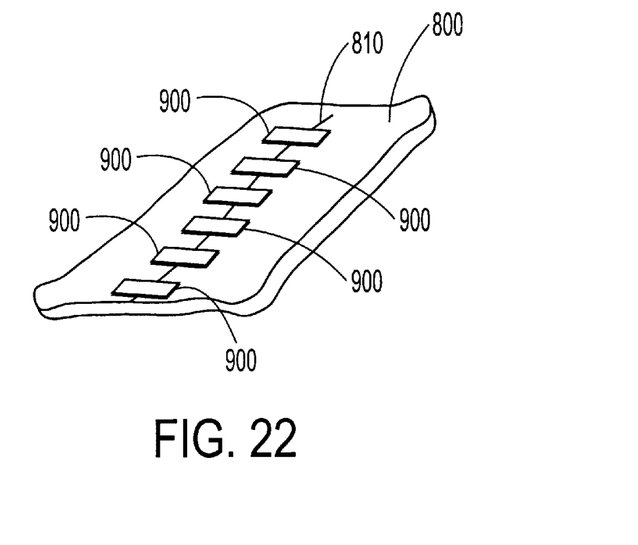
FIG. 22 shows a partial view of a target tissue having a plurality of strips of adhesive applied by the applicator.

Depending on the size and length of the incision or wound, it may be necessary to provide several such strips of adhesive, as shown in FIG. 22. As mentioned earlier, the hand-held applicator can include various applicator tips 400, such as fine tips, broad tips or a spray tip that can be adapted to apply a suitably sized strip of adhesive to the incision or wound 810.

Monomers that may be used in this invention are preferably readily polymerizable, e.g. anionically polymerizable or free radical polymerizable, to form polymers. Such monomers include those that form polymers, which may, but do not need to, biodegrade. Reference is made, for example, to U.S. Pat. No. 5,328,687, which is hereby incorporated by reference herein. As defined herein, "histotoxicity" refers to adverse tissue response, such as inflammation due to the presence of toxic materials in the tissue.

1,1-disubstituted ethylene monomers that can be used in conjunction with the device include, but are not limited to, monomers of the formula:

$$HRC=CXY \qquad (I)$$

wherein X and Y are each strong electron withdrawing groups, and R is H, —CH=CH$_2$ or, provided that X and Y are both cyano groups, a C$_1$–C$_4$ alkyl group.

Examples of monomers within the scope of formula (I) include alpha-cyanoacrylates, vinylidene cyanides, C$_1$–C$_4$ alkyl homologues of vinylidene cyanides, dialkyl methylene malonates, acylacrylonitriles, vinyl sulfinates and vinyl sulfonates of the formula CH$_2$=CX'Y' wherein X' is —SO$_2$R' or —SO$_3$R' and Y' is —CN, —COOR', —COCH$_3$, —SO$_2$R' or —SO$_3$R', and R' is H or hydrocarbyl.

Preferred monomers of formula (I) for use in this invention are alpha-cyanoacrylates. These monomers are known in the art and have the formula $$HR^2C=C\begin{array}{c}CN\\COOR^3\end{array} \qquad (II)$$

wherein R$^2$ is hydrogen and R$^3$ is a hydrocarbyl or substituted hydrocarbyl group; a group having the formula —R$^4$—O—R$^5$—O—R$^6$, wherein R$^4$ is a 1,2-alkylene group having 2–4 carbon atoms, R$^5$ is an alkylene group having 2–4 carbon atoms, and R$^6$ is an alkyl group having 1–6 carbon atoms; or a group having the formula $$—R^7—\underset{\underset{O}{\|}}{C}—O—R^8,$$

wherein R$^7$ is one of the following: 1) —CH$_2$, 2)—CH (CH$_3$)—, or 3)—C(CH$_3$)$_2$— wherein n is 1–10, preferably 1–5, and R$^8$ is an organic moiety.

Examples of suitable hydrocarbyl and substituted hydrocarbyl groups include straight chain or branched chain alkyl groups having 1–16 carbon atoms; straight chain or branched chain C$_1$–C$_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic moiety R$^8$ may be substituted or unsubstituted and may be straight chain, branched or cyclic, saturated, unsaturated or aromatic. Examples of such organic moieties include C$_1$–C$_8$ alkyl moieties, C$_2$–C$_8$ alkenyl moieties, C$_2$–C$_8$ alkynyl moieties, C$_3$–C$_{12}$ cycloaliphatic moieties, aryl moieties such as phenyl and substituted phenyl and aralkyl moieties such as benzyl, methylbenzyl and phenylethyl. Other organic moieties include substituted hydrocarbon moieties, such as halo (e.g., chloro-, fluoro- and bromo-substituted hydrocarbons) and oxy- (e.g., alkoxy substituted hydrocarbons) substituted hydrocarbon moieties. Preferred organic radicals are alkyl, alkenyl and alkynyl moieties having from 1 to about 8 carbon atoms, and halo-substituted derivatives thereof. Particularly preferred are alkyl moieties of 4 to 6 carbon atoms.

In the cyanoacrylate monomer of formula (II), $R^3$ is preferably an alkyl group having 1–10 carbon atoms or a group having the formula —$AOR^9$, wherein A is a divalent straight or branched chain alkylene or oxyalkylene moiety having 2–8 carbon atoms, and $R^9$ is a straight or branched alkyl moiety having 1–8 carbon atoms.

Examples of groups represented by the formula —$AOR^9$ include 1-methoxy-2-propyl, 2-butoxy ethyl, isopropoxy ethyl, 2-methoxy ethyl, and 2ethoxy ethyl.

Preferred alpha-cyanoacrylate monomers useful in this invention include 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, and 1-methoxy-2-propyl cyanoacrylate.

The alpha-cyanoacrylates of formula (II) can be prepared according to methods known in the art. Reference is made, for example, to U.S. Pat. Nos. 2,721,858 and 3,254,111, each of which is hereby incorporated by reference herein. For example, the alpha cyanoacrylates can be prepared by reacting an alkyl cyanoacetate with formaldehyde in a non-aqueous organic solvent and in the presence of a basic catalyst, followed by pyrolysis of the anhydrous intermediate polymer in the presence of a polymerization inhibitor. The alpha-cyanoacrylate monomers prepared with low moisture content and essentially free of impurities are preferred for biomedical use.

The alpha-cyanoacrylates of formula (II) wherein $R^3$ is a group having the formula —$R^4$—O—$R^5$—O—$R^6$ can be prepared according to the method disclosed in U.S. Pat. No. 4,364,876 to Kimura et al., which is hereby incorporated by reference herein. In the Kimura et al. method, the alpha-cyanoacrylates are prepared by producing a cyanoacetate by esterifying cyanoacetic acid with an alcohol or by transesterifying an alkyl cyanoacetate and an alcohol; condensing the cyanoacetate and formaldehyde or para-formaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The alpha-cyanoacrylates of formula (II) wherein $R^3$ is a group having the formula can be prepared according to the procedure described in U.S. Pat. No. 3,995,641 to Kronenthal et al., which is hereby incorporated by reference herein. In the Kronenthal et al. method, such alpha-cyanoacrylate monomers are prepared by reacting an alkyl ester of an alpha-cyanoacrylic acid with a cyclic 1,3-diene to form a Diels-Alder adduct which is then subjected to alkaline hydrolysis followed by acidification to form the corresponding alpha-cyanoacrylic acid adduct. The alpha-cyanoacrylic acid adduct is preferably esterified by an alkyl bromoacetate to yield the corresponding carbalkoxymethyl alpha-cyanoacrylate adduct. Alternatively, the alpha-cyanoacrylic acid adduct may be converted to the alpha-cyanoacrylyl halide adduct by reaction with thionyl chloride. The alpha-cyanoacrylyl halide adduct is then reacted with an alkyl hydroxyacetate or a methyl substituted alkyl hydroxyacetate to yield the corresponding carbalkoxymethyl alpha-cyanoacrylate adduct or carbalkoxy alkyl alpha-cyanoacrylate adduct, respectively. The cyclic 1,3-diene blocking group is finally removed and the carbalkoxy methyl alpha-cyanoacrylate adduct or the carbalkoxy alkyl alpha-cyanoacrylate adduct is converted into the corresponding carbalkoxy alkyl alpha-cyanoacrylate by heating the adduct in the presence of a slight deficit of maleic anhydride.

Examples of monomers of formula (II) include cyanopentadienoates and alpha-cyanoacrylates of the formula:

(III)

wherein Z is —CH=$CH_2$ and $R^3$ is as defined above. The monomers of formula (III) wherein $R^3$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is hereby incorporated by reference herein.

Preferred monomers are alkyl alpha-cyanoacrylates and more preferably octyl alpha-cyanoacrylates, especially 2-octyl alpha-cyanoacrylate. Monomers utilized in the present application should be very pure and contain few impurities (e.g., surgical grade).

Compositions that are useful in the present invention may include at least one plasticizing agent that imparts flexibility to the polymerized monomer formed on the wound or incision. The plasticizing agent preferably contains little or no moisture and should not significantly affect the polymerization of the monomer.

Examples of suitable plasticizers include acetyl tributyl citrate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

Compositions useful in the present invention may also include at least one acidic stabilizing agent that inhibits polymerization. Such stabilizing agents may also include mixtures of anionic stabilizing agents and radical stabilizing agents.

Examples of suitable anionic stabilizing agents include, but are not limited to, sulfones (e.g., α-chloro-α-hydroxy-o-toluenesulfonic acid-γ-sulfone), sulfur dioxide, sulfuric acid, sulfonic acid, lactone, boron trifluoride, organic acids, such as acetic acid or phosphoric acid, alkyl sulfate, alkyl sulfite, 3-sulfolene, alkylsulfone, alkyl sulfoxide, mercaptan, and alkyl sulfide and mixtures thereof. Preferable anionic stabilizing agents are acidic stabilizing agents of organic acids such as acetic acid or phosphoric acid. In embodiments, the amount of sulfur dioxide stabilizer is less than 100 ppm, preferably 5–75 ppm, and more preferably from about 20–50 ppm. The amount of sulfone and/or trifluoracetic acid is about 500–3000 ppm.

Examples of suitable radical stabilizing agents include hydroquinone, hydroquinone monomethyl ether, catechol, pyrogallol, benzoquinone, 2-hydroxybenzoquinone, p-methoxy phenol, t-butyl catechol, butylated hydroxy anisole (BHA), butylated hydroxy toluene, and t-butyl hydroquinone. In embodiments, the amount of BHA is about 1,000–5,000 ppm.

Suitable acidic stabilizing agents include those having aqueous $pK_a$ ionization constants ranging from −12 to 7, about −5 to about 7, preferably from about −3.5 to about 6, and more preferably from about 2 to about 5.5. For example, suitable acidic stabilizing agents include: hydrogen sulfide ($pK_a$ 7.0), carbonic acid ($pK_a$ 6.4), triacetylmethane ($pK_a$ 5.9), acetic acid ($pK_a$ 4.8), benzoic acid ($pK_a$ 4.2), 2,4-dinitropheniol ($pK_a$ 4.0), formic acid ($pK_a$ 3.7), nitrous acid ($pK_a$ 3.3), hydrofluoric acid ($pK_a$ 3.2), chloroacetic acid ($pK_a$ 2.9), phosphoric acid ($pK_a$ 2.2), dichloroacetic acid ($pK_a$ 1.3), trichloroacetic acid ($pK_a$ 0.7), 2,4,6-trinitrophenol (picric acid) ($pK_a$ 0.3), trifluoroacetic acid ($pK_a$ 0.2), sulfuric acid ($pK_a$ −3.0) and mixtures thereof. In embodiments, the amount of trifluoroacetic acid is about 500–1,500 ppm.

When adding the above-mentioned acidic stabilizing agents to the adhesive composition, the addition of plasticizing agents in amounts ranging from about 0.5 wt. % to about 16 wt. %, preferably from about 3 wt. % to about 9 wt. %, and more preferably from about 5 wt. % to about 7 wt. % provides increased elongation and toughness of the polymerized monomer over polymerized monomers having amounts of plasticizing agents and acidic stabilizing agents outside of the above ranges.

The concentration of the acidic stabilizing agents utilized may vary depending on the strength of the acid. For example, when using acetic acid, a concentration of 80–200 ppm (wt/wt), preferably 90–180 ppm (wt/wt), and more preferably 100–150 ppm (wt/wt) may be utilized. When using a stronger acid such as phosphoric acid, a concentration range of 20–80 ppm (wt/wt), preferably, 30–70 ppm (wt/wt) and more preferably 40–60 ppm (wt/wt) may be utilized. In embodiments, the amount of trifluoroacetic acid is about 100 to 3000 ppm, preferably 500–1500 ppm. In other embodiments, the amount of phosphoric acid is about 10–200 ppm, preferably about 50–150 ppm, and more preferably about 75–125 ppm.

Other suitable stabilized monomer adhesive compositions can be found in co-pending U.S. application Ser. No. 09/099,457 filed Jun. 18, 1998, the disclosure of which is incorporated by reference herein in its entirety.

Other compositions that are useful in conjunction with the present device are exemplified by U.S. Pat. Nos. 5,624,669, 5,582,834, 5,575,997, 5,514,371, 5,514,372, 5,259,835 and 5,328,687, incorporated by reference herein in their entirety. Compositions that are useful in conjunction with the device of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites; ammonium sulfite salts; amines; amides; imides; nitrites; carbamates; alcohols; mercaptans; proteins; mixtures of amines, amides, and proteins; active methylene compounds such as cyclic ketones and compounds having a b-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, where the atom is directly bonded by a double bond to another carbon or nitrogen atom.

Bisulfites and sulfites useful as the formaldehyde scavenger compound in this invention include alkali metal salts such as lithium, sodium and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like.

Examples of amines useful in this invention include the aliphatic and aromatic amines such as, for example, aniline, benzidine, aminopyrimidine, toluene-diamine, triethylenediamine, diphenylamine, diaminodiphenylamine, hydrazines and hydrazide.

Suitable proteins include collagen, gelatin, casein, soybean protein, vegetable protein, keratin and glue. The preferred protein for use in this invention is casein.

Suitable amides for use in this invention include urea, cyanamide, acrylamide, benzamide, and acetamide. Urea is a preferred amide.

Suitable alcohols include phenols, 1,4-butanediol, d-sorbitol, and polyvinyl alcohol.

Examples of suitable compounds having a b-dicarbonyl group include malonic acid, acetylacetone, ethylacetone, acetate, malonamide, diethylmalonate or another malonic ester.

Preferred cyclic ketones for use in this invention include cyclohexanone or cyclopentanone.

Examples of suitable heterocyclic compounds for use as the formaldehyde scavenger in this invention are disclosed, for example, in U.S. Pat. No. 4,127,382 (Perry) which is hereby incorporated by reference herein. Such heterocyclic compounds include, for example, benzimidazole, 5-methyl benzimidazole, 2-methylbenzimidazole, indole, pyrrole, 1,2,4-triazole, indoline, benzotriazole, indoline, and the like.

A preferred formaldehyde scavenger for use in this invention is sodium bisulfite.

In formulating a composition that is useful in conjunction with the device of the present invention, the formaldehyde concentration reducing agent, e.g., formaldehyde scavenger compound, is added in an effective amount to the cyanoacrylate. The "effective amount" is that amount sufficient to reduce the amount of formaldehyde generated during subsequent in vivo biodegradation of the polymerized cyanoacrylate. This amount will depend on the type of active formaldehyde concentration reducing agent, and can be readily determined without undue experimentation by those skilled in the art.

The formaldehyde concentration reducing agent that may be used in a composition useful in conjunction with the device of this invention may be in either free form or in microencapsulated form. Other compositions useful in this invention are exemplified in U.S. patent Application Ser. No. 08/714,288, incorporated by reference herein in its entirety.

When microencapsulated, the formaldehyde concentration reducing agent is released from the microcapsule continuously over a period of time during the in vivo biodegradation of the cyanoacrylate polymer.

For purposes of this invention, the microencapsulated form of the formaldehyde concentration reducing agent is preferred because this embodiment prevents or substantially reduces polymerization of the cyanoacrylate monomer by the formaldehyde concentration reducing agent, which increases shelf-life and facilitates handling of the monomer composition during use.

Microencapsulation of the formaldehyde scavenger can be achieved by many known microencapsulation techniques. For example, microencapsulation can be carried out by dissolving a coating polymer in a volatile solvent, e.g., methylene chloride, to a polymer concentration of about 6% by weight; adding a formaldehyde scavenger compound in particulate form to the coating polymer/solvent solution under agitation to yield a scavenger concentration of 18% by weight; slowly adding a surfactant-containing mineral oil solution to the polymer solution under rapid agitation; allowing the volatile solvent to evaporate under agitation; removing the agitator; separating the solids from the mineral oil; and washing and drying the microparticles. The size of the microparticles will range from about 0.001 to about 1000 microns.

The coating polymer for microencapsulating the formaldehyde concentration reducing agent should be polymers which undergo in vivo bioerosion, preferably at rates similar to or greater than the cyanoacrylate polymer formed by the monomer, and should have low inherent moisture content Such bioerosion can occur as a result of the physical or chemical breakdown of the encapsulating material, for example, by the encapsulating material passing from solid to solute in the presence of body fluids, or by biodegradation of the encapsulating material by agents present in the body.

Examples of coating materials which can be used to microencapsulate the formaldehyde concentration reducing agent include polyesters, such as polyglycolic acid, polylactic acid, poly-1,4-dioxa-2-one, polyoxaltes, polycarbonates, copolymers of polyglycolic acid and polylactic acid, polycaprolactone, poly-b-hydroxybutyrate, copolymers of epsilon-caprolactone and delta-valerolactone, copolymers of epsilon-caprolactone and DL-dilactide, and polyester hydrogels; polyvinylpyrrolidone; polyamides; gelatin; albumin; proteins; collagen; poly(orthoesters); poly (anhydrides); poly(alkyl-2-cyanoacrylates); poly (dihydropyrans); poly(acetals); poly(phosphazenes); poly (urethanes); poly(dioxinones); cellulose; and starches.

Examples of the surfactant which can be added to the mineral oil include those commercially available under the designations Triton x-100™ (Rohm and Hass)(octoxynol), Tween 20 (ICI Americas)(polysorbate) and Tween 80 (ICI Americas)(polysorbate).

Compositions useful in conjunction with the device of this invention may further contain one or more adjuvant substances, such as thickening agents, medicaments, or the like, to improve the medical utility of the monomer for particular medical applications.

Suitable thickeners include, for example, polycyanoacrylates, polylactic acid, poly-1,4-dioxa-2-one, polyoxalates, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene. Examples of alkyl methacrylates and acrylates are poly(2-ethylhexyl methacrylate) and poly(2-ethylhexyl acrylate), also poly(butylmethacrylate) and poly(butylacrylate), also copolymers of various acrylate and methacrylate monomers, such as poly (butylmethacrylate-co-methylacrylate).

To improve the cohesive strength of adhesives formed from the compositions useful in this invention, difunctional monomeric cross-linking agents may be added to the monomer compositions of this invention. Such crosslinking agents are known in the art, and are disclosed, for example, in U.S. Pat. No. 3,940,362 to Overhults, which is hereby incorporated by reference herein. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoacrylates). A catalytic amount of an amine activated free radical initiator or rate modifier may be added to initiate polymeriztion or to modify the rate of polymerization of the cyanoacrylate monomer/crosslinking agent blend.

In embodiments, the adhesive compositions may additionally contain heat and/or light (e.g., visible or ultraviolet light) activated initiators and accelerators that initiate crosslinking of cyanoacrylate compositions containing compounds of formula (I).

Particular initiators for particular systems may be readily selected by one of ordinary skill in the art without undue experimentation. Suitable polymerization initiators for the cyanoacrylate compositions include, but are not limited to, detergent compositions; surfactants: e.g., nonionic surfactants such as polysorbate 20 (e.g., Tween 20™), polysorbate 80 (e.g., Tween 80™) and poloxamers, cationic surfactants such as tetrabutylammonium bromide, anionic surfactants such as benzalkonium chloride or its pure components, stannous octoate (tin (II) 2-ethylheaxanoate), and sodium tetradecyl sulfate, and amphoteric or zwitterionic surfactants such as dodecyldimethyl(3-sulfopropyl)ammonium hydroxide, inner salt; amines, imines and amides, such as imidazole, tryptamine, urea, arginine and povidine; phosphines, phosphites and phosphonium salts, such as triphenylphosphine and triethyl phosphite; alcohols such as ethylene glycol, methyl gallate, ascorbic acid, tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat 336; and organometallics and manganese acetylacetonate and radical initiators. Cobalt naphthenate can be used as an accelerator for peroxide.

Compositions useful in conjunction with the device of the present invention may further contain fibrous reinforcement and colorants, e.g., dyes and pigments. Examples of suitable fibrous reinforcement include PGA microfibrils, collagen microfibrils, cellulosic microfibrils, and olefinic microfibrils. Examples of suitable colorants include 1-hydroxy-4-[4-methylphenyl-amino]-9,10 anthracenedione (D+C violet No. 2); disodium salt of 6-hydroxy-5-[(4-sulfophenyl)axo]-2-naphthalene-sulfonic acid (FD+C Yellow No. 6); 9-(o- carboxyphenyl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo-1H-indole-5-sulfonic acid disodium salt (FD+C Blue No. 2); and [phthalocyaninato (2-)] copper.

Other compositions useful in the present invention are disclosed in U.S. Pat. Nos. 5,259,835, 5,624,669, 5,328,687, 5,928,611 and U.S. patent applications Ser. Nos. 08/609,921, 08/714,288, 08/909,845, 08/755,007, 08/920,876, 09/025,473, and 09/099,457, all of which are incorporated by reference herein in their entirety.

What is claimed is:

1. A hand-held applicator for laparoscopic or endoscopic surgery, comprising:

a base grippable by a hand of an operator;

a pump;

a tubular extension connected at a proximal end to the base, the tubular extension having an outer diameter small enough to fit within a laparoscopic pathway or trocar, an inner bore in fluid communication with the pump, and a length sufficient to extend beyond the laparoscopic pathway or trocar; and a tip attachable to a distal end of the tubular extension, the tip when attached being in fluid communication with the inner bore and containing a predetermined amount of a liquid or semi-liquid composition to be dispensed, wherein the pump allows for precise delivery of the composition without physically contacting the composition by acting on the inner bore to transfer pressure from the pump to the liquid or semi-liquid composition to be dispersed.

2. The hand-held applicator of claim 1, wherein the hand-held applicator is a pipetter.

3. The hand-held applicator of claim 2, wherein the pipetter is a digital pipetter.

4. The hand-held applicator of claim 1, wherein the hand-held applicator is a repeat pipetter.

5. The hand-held applicator of claim 2, wherein the tip contains a volume of between 1 and 10000 μL of the composition.

6. The hand-held applicator of claim 2, wherein the tip contains a volume of between 200 and 2000 μL of the composition.

7. The hand-held applicator of claim 1, wherein the composition is an adhesive.

8. The hand-held applicator of claim 7, wherein the adhesive is a 1,1-disubstituted ethylene adhesive.

9. The hand-held applicator of claim 7, wherein the adhesive is an α-cyanoacrylate.

10. The hand-held applicator of claim 1, wherein the hand-held applicator is resterilizable.

11. The hand-held applicator of claim 1, wherein the pump comprises a plunger located within the base and an actuator element that moves the plunger, the actuator element extending from the base and actuatable by a finger or thumb of the hand of the operator gripping the base.

12. The hand-held applicator of claim 1, wherein the tip is formed from polyethylene.

13. The hand-held applicator of claim 1, wherein the tip has a distal opening with a broad width so as to apply a bead of several mm of the composition.

14. The hand-held applicator of claim 1, wherein the tip has a distal opening with a fine width so as to apply a fine bead of up to about 0.5 mm of the composition.

15. The hand-held applicator of claim 1, wherein the tip is shaped to provide delivery of the composition in a fine spray.

16. The hand-held applicator of claim 1, wherein the tip has a distal opening containing a porous body impregnated with a polymerization initiator or rate modifier.

17. The hand-held applicator of claim 1, wherein the tip has a length of between 1.27 to 7.62 cm.

18. The hand-held applicator of claim 1, wherein the tubular delivery element is sized to fit into a 5 mm diameter trocar.

19. The hand-held applicator of claim 1, wherein the tubular extension has a length of between 15 to 61 cm.

20. The hand-held applicator of claim 1, wherein the tubular extension is removably attached to the base by a luer lock fitting.

21. The hand-held applicator of claim 1, wherein the tip is removably attached to the distal end of the tubular assembly by a friction fit.

22. The hand-held applicator of claim 1, wherein the hand-held applicator is sterile.

23. The hand-held applicator of claim 1, further comprising a wound closure device including at least two wound closure pins operable at a distal end of said tubular extension and a manipulation element mechanically coupled to the at least two wound closure pins through a connecting element, the manipulation element being operable by the hand of the operator.

24. The hand-held applicator of claim 23, further comprising a second tubular extension arranged substantially parallel to and adjacent the first tubular extension, the wound closure pins and connecting element being provided closely adjacent the first tubular extension.

25. The hand-held applicator of claim 24, wherein the second tubular extension is coaxially arranged relative to the tubular extension and the wound closure pins and the connecting element are provided in a space between the tubular extension and the second tubular extension.

26. A method of applying a composition to tissue within a body during laparoscopic or endoscopic surgery, comprising the steps of:

inserting the tubular extension and tip of the hand-held applicator of claim 1 into the body through a laparoscopic pathway or trocar;

positioning the tip adjacent target tissue within the body;

actuating the pump to controllably dispense the composition onto the tissue through the tip; and removing the tubular extension and tip from the laparoscopic pathway or trocar.

27. The method of claim 26, further comprising the steps of:

removing and discarding the removably attachable tip from the tubular assembly after use; and attaching a new tip onto the tubular assembly.

28. The method of claim 26, further comprising the step of:

discarding the hand-held applicator after a single use.

29. The method of claim 26, wherein the composition being dispensed is an adhesive.

30. The method of claim 29, wherein the adhesive is a 1,1-disubstituted ethylene adhesive.

31. The method of claim 29, wherein the adhesive is an alpha-cyanoacrylate.

32. A kit comprising a saleable package containing the hand-held applicator of claim 1.

33. The kit of claim 32, wherein said package contains a plurality of said tips.

34. The kit of claim 33, wherein said plurality of said tips are of more than one size.

35. The kit of claim 32, wherein said kit further contains a trocar.

36. The kit of claim 32, wherein the contents of the kit are sterile.

37. The kit of claim 32, wherein the composition in the tip is an adhesive.

38. The kit of claim 37, wherein the adhesive is a 1,1-disubstituted ethylene adhesive.

39. The kit of claim 37, wherein the adhesive is an alpha-cyanoacrylate adhesive.

40. The kit of claim 37, wherein the tip has a distal opening containing a porous body having on or in it a polymerization initiator or rate modifier.

41. A method of applying a composition to tissue within a body during laparoscopic or endoscopic surgery, comprising the steps of:

inserting the tubular extension and tip of the hand-held applicator of claim 23 into the body through a laparoscopic pathway or trocar;

positioning the tip adjacent target tissue within the body;

engaging the wound closure pins with target tissue adjacent a wound or incision;

aligning and closing the wound or incision by manipulating the wound closure pins with the manipulation element;

actuating the pump to controllably dispense the composition onto the tissue through the tip; and removing the tubular extension and tip from the laparoscopic pathway or trocar.

42. The method of claim 41, further comprising the step of disengaging the wound closure pins from the target tissue and fully retracting the wound closure pins.

43. The method of claim 41, wherein the pump is actuated to controllably dispense the composition onto the tissue through the tip before engaging the wound closure pins with the target tissue.

44. The method of claim 41, wherein the pump is actuated to controllably dispense the composition onto the tissue through the tip after engaging the wound closure pins with the target tissue.

45. A hand-held applicator and wound closure device for laparoscopic or endoscopic surgery, comprising:

a base grippable by a hand of an operator;

a pump;

a tubular extension connected at a proximal end to the base and in fluid communication with the pump, the tubular extension having an outer diameter small enough to fit within a laparoscopic pathway or trocar and a length sufficient to extend beyond the laparoscopic pathway or trocar, a tip attachable to a distal end of the tubular extension, the tip containing a predetermined amount of a liquid or semi-liquid composition to be dispensed; and a wound closure device including at least two wound closure pins operable at a distal end of said tubular extension and a manipulation element mechanically coupled to the at least two wound closure pins through a connecting element, the manipulation element being operable by the hand of the operator.

* * * * *